United States Patent [19]

Conti

[11] Patent Number: 5,254,540
[45] Date of Patent: Oct. 19, 1993

[54] SACCHARIDE COPOLYMERS HAVING ANTIBACTERIAL ACTIVITY

[75] Inventor: Franco Conti, Milan, Italy

[73] Assignee: Etablissement Texcontor, Liechtenstein

[21] Appl. No.: 447,846

[22] Filed: Dec. 8, 1989

[30] Foreign Application Priority Data

Jul. 21, 1989 [IT] Italy ................. 21262 A/89

[51] Int. Cl.$^5$ ................. A61K 31/715; C07H 17/00; C08B 1/00; C08B 31/00

[52] U.S. Cl. ........................... 514/57; 514/60; 536/17.2; 536/17.3; 536/17.4; 536/18.7; 536/30; 536/45

[58] Field of Search ............. 514/57, 54, 55, 58, 514/59, 60; 536/17.2, 17.3, 17.4, 17.9, 18.7, 20, 30, 45, 46, 51, 52, 55.3

[56] References Cited

U.S. PATENT DOCUMENTS

| | | | |
|---|---|---|---|
| 3,691,152 | 9/1972 | Vemuri | 536/114 |
| 4,254,257 | 3/1981 | Schroeck | 536/55.1 |
| 4,436,731 | 3/1984 | Maltz | 536/20 |
| 4,675,394 | 6/1987 | Solarek et al. | 536/4.1 |
| 4,758,282 | 7/1988 | Stober et al. | 536/114 |
| 4,792,415 | 12/1988 | Colegrove | 536/114 |
| 4,898,915 | 2/1990 | Harwood et al. | 525/376 |
| 4,952,684 | 8/1990 | Yalpani et al. | 536/18.7 |
| 4,959,461 | 9/1990 | Yalpani et al. | 536/55.3 |
| 4,963,664 | 10/1990 | Yalpani et al. | 536/18.7 |
| 4,985,410 | 1/1991 | Conti | 514/57 |

FOREIGN PATENT DOCUMENTS 1176985 10/1984 Canada .

*Primary Examiner*—Johnnie R. Brown
*Assistant Examiner*—Everett White
*Attorney, Agent, or Firm*—Birch, Stewart, Kolasch & Birch

[57] ABSTRACT

Saccharide copolymers having antibacterial activity obtained by copolymerization of an oligosaccharide or polysaccharide with a nitrogen containing vinyl derivative, quaternarization of the obtained copolymer followed by oxidation of the oligosaccharide or polysaccharide monomer unit with formation of the corresponding dialdehyde.

2 Claims, No Drawings

SACCHARIDE COPOLYMERS HAVING ANTIBACTERIAL ACTIVITY

PRIOR ART

Disinfectant and antiseptic products containing quaternary ammonium compounds, which exert an antibacterial activity against gram-positive and gram-negative bacteria and against fungi and viruses are known. Such compounds, however, show a high toxicity and particularly, when administered orally, may cause nausea, vomiting, muscular paralysis with possible respiratory muscle block and ensuing asphyxia.

Saccharide copolymers containing quaternary ammonium groups and exerting antibacterial activity, which are substantially non-toxic are also known (EP 0042075).

SUMMARY OF THE INVENTION

We have now found new saccharide copolymers which possess an activity spectrum much broader than that of known copolymers, and which, in particular exert an activity which may be up to ten times greater against mycetes and yeasts, and are practically free of toxicity.

Said copolymers have the following formula (I)

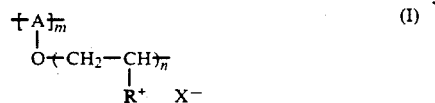

(I)

where

A represents oligosaccharide or polysaccharide monomeric units, some of which contain two aldehyde groups;

m is an integer between 10 and 10,000;

$R^+$ is a quaternary ammonium compound radical selected from the group comprising

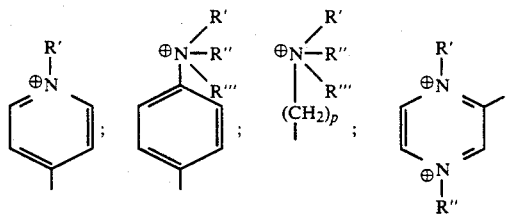

where $R'$, $R''$ and $R'''$, equal or different, are alkyl or benzyl radicals and p is zero or an integer between 1 and 10; $X^-$ is an anion selected from the groups comprising $F^-$, $Cl^-$, $Br^-$, $I^-$, $HSO_4^-$, $CH_3OSO_3^-$;

n is an integer between 100 and 250.

Said copolymers are prepared through a process comprising the following steps:

a) copolymerization of an oligosaccharide or polysaccharide with a nitrogen containing vinyl derivative;

b) quaternarization of the copolymer obtained in a);

c) oxidation of the oligosaccharide or polysaccharide monomer unit with formation of the corresponding dialdehyde.

DETAILED DESCRIPTION OF THE INVENTION

The characteristics and advantages of the copolymers according to the present invention and of their preparation process will be further illustrated in the following detailed description.

The invention refers to copolymers having the following formula:

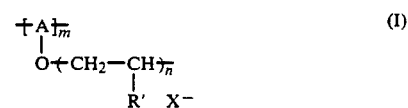

(I)

where

A represents oligosaccharide or polysaccharide monomeric units, some of which contain two aldehyde groups;

m is an integer between 10 and 10,000;

$R^+$ is a quaternary ammonium compound radical selected from the group comprising

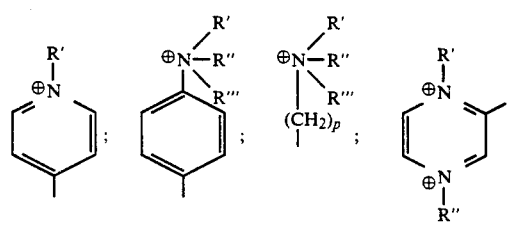

where $R'$, $R''$ and $R'''$, equal or different, are alkyl or benzyl radicals and p is zero or an integer between 1 and 10; $X^-$ is an anion selected from the group comprising $F^-$, $Cl^-$, $Br^-$, $I^-$, $HSO_4^-$ and $CH_3OSO_3^-$;

n is an integer between 100 and 250.

The A monomer units are monomer units of natural oligosaccharides or polysaccharides, which contain or do not contain nitrogen atoms, or of cellulose derivatives.

Of said monomer units a percentage of between 10 and 90% contains two aldehyde groups obtained by oxidative opening in the $C_2$ and $C_3$ positions of the glucoside unit. More particularly, said percentage of monomer units containing two aldehyde groups may be between 20 and 90%.

Said monomeric units have e.g. the following structure:

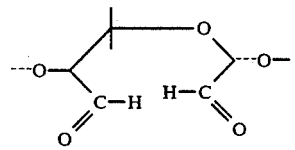

The preparation of the copolymers having formula (I) according to the present invention is carried out through the following steps:

a) copolymerization of an oligosaccharide or polysaccharide with a suitable nitrogen containing vinyl derivative.

This step is carried out in water or in aqueous/organic solvent in the presence of polymerization initiators such as $Fe^{II}/H_2O_2$, $Na_2S_2O_4/H_2O_2$, $Ce^{IV}/HNO_3$, $Ce^{IV}/H_2SO_4$, transition metal salts and other suitable initiators.

The reaction takes place at a temperature below 40° C. for times comprised between 3 and 48 hours.

The homopolymer which may be formed is removed by extraction of the product with a suitable solvent.

The preferred vinyl derivative employed in the copolymerization is 4-vinylpyridine; however, one can employ also compounds such as 4-vinylaniline, allylamine and vinyl pyrazine.

b) Quaternarization of the copolymer obtained in a): in this step alkylating agents selected according to the alkyl group desired in the quaternary ammonium group and compatible with the general copolymer structure are employed.

Generally alkyl halides are employed and among them preferably ethyl bromide and methyl iodide.

The reaction takes place in a solvent having a high dielectric constant, such as methanol, nitrobenzene, DMF, THF and sulfolane, at the boiling point, under reflux;

c) Dialdehyde formation.

This step takes place by treating the product of step b) with an oxidizing agent such as sodium periodate or lead tetracetate, in the first case in water and in the second case in an organic solvent, such as benzene or methanol.

The reaction is carried out at a temperature below 40° C. for a period between 2 and 16 hours.

The copolymers of the present invention assayed in biological tests show a high, wide spectrum antibacterial activity and low toxicity.

In particular, they show vis-a-vis yeasts and mycetes an activity which may be even ten times higher, compared to known antibacterial saccharide copolymers.

The copolymers according to the present invention may be employed as active substances for the preparation of substances having antibacterial activity, in admixture with the diluents, solvents and excipients normally employed in the pharmaceutical praxis.

The following examples are given for illustrative, non-limitative purposes.

EXAMPLE 1 a) Copolymerization:

50.0 g corn starch are suspended in 500 ml water and the suspension is heated to the boiling point. After cooling, 63% $HNO_3$ is added to obtain a 1.5N $HNO_3$ solution. Air is removed from the solution by passing a nitrogen stream for the duration of 30 minutes, and 100 ml 4-vinylpyridine are added. An amount of $Ce^{IV}$ Ammonium nitrate is then added to the solution up to a 0.01M $Ce^{IV}$ concentration. After stirring for 12 hours at room temperature, the solution is made alkaline by addition of a 3:1 10% NaOH -1,2 propandiol mixture.

The formed precipitate is separated and washed until disappearance of starch in the washing water.

IR Analysis: Typical bands: 1600 $cm^{-1}$, 1220 $cm^{-1}$, 1070 $cm^{-1}$, 820 $cm^{-1}$.

Elemental analysis: C=52.78%; M=4.82%.

b) Quaternarization

This step takes place by suspending 70 g of the copolymer obtained in a) in 500 ml methanol and 100 ml ethyl bromide.

After heating on reflux for 120 minutes and cooling, the solvent and the excess reagent are removed by evaporation to dryness.

IR analysis: typical bands: 1600 $cm^{-1}$.

Elemental analysis: Br=39.80%.

c) Dialdehyde formation:

30 g of the product obtained under b) are dissolved in 150 ml distilled water and 7.0 g sodium periodate (0.03272 moles) are added to the solution in three portions, one every 2 hours. The maximum temperature reached is 40° C. The solution is kept under stirring for 16 hours in the darkness.

10 ml ethylene glycol are added to destroy the excess of sodium periodate and then the solution is dialyzed against distilled water until all salts are eliminated.

The thus obtained solution is then lyophilized - 25.0 g dry product are obtained.

The aldehyde content, determined on the dry, lyophilized product by the hydroxylamine hydrochloride method is 1.95 meq/g of product (5.65%).

IR analysis: 2700 $cm^{-1}$; 1705 $cm^{-1}$, in addition to pre-existing bands.

Elemental analysis: Br=40.0%.

EXAMPLE 2 a) Copolymerization: as in Example 1
b) Quaternarization: as in Example 1
c) Dialdehyde formation:

30 g of the product obtained in b) are suspended in 100 ml benzene and 14.5 g solid lead tetra-acetate are added in small portions to the suspension, taking care to keep the temperature below 40° C. After stirring for 16 hours, 10 ml ethylene glycol are added, and, after 2 hours of further stirring, the mixture is filtered.

The solid is dissolved in 100 ml water and dialysis of the solution is carried out against distilled water. The solution, free of inorganic salts, is then lyophilized.

27.0 g of dry product are obtained.

Chemical analysis: Aldehyde content: 1.90 meq/g (5.51%).

IR analysis: 2700 $cm^{-1}$, 1700 $cm^{-1}$ in addition to the pre-existing bands.

Elemental analysis: Br=39.5%.

EXAMPLE 3 a) Copolymerization as in Example 1
b) Quaternarization as in Example 1
c) Dialdehyde formation 30 g of the quaternarized product are suspended in 150 ml methanol and 14.5 g lead tetra-acetate (0.0327 moles) and 0.27 g trichloroacetic acid (0.00163 moles) are added.

The solution is kept at 25° C. for 2 hours under stirring and the solid is then filtered and then washed with 100 ml methanol.

The solid obtained is dissolved in 100 ml distilled water and dialyzed.

The solid product is recovered from the solution by lyophilization. 26.2 g dry product are obtained.

Chemical analysis: Aldehyde contents=20 meq/g (5.8%).

IR analysis: 2700 $cm^{-1}$, 1700 $cm^{-1}$, in addition to the pre-existing bands.

Elemental analysis: Br=40.1%.

EXAMPLE 4 a) Copolymerization as in Example 1
b) Quaternarization as in Example 1
c) Dialdehyde formation:

30 g of the quaternarized product, obtained starting from hydroxyethyl cellulose, are dissolved in 150 ml distilled water.

7.0 g solid sodium periodate (0.03272 moles) are added to the solution in 3 portions. The maximum temperature reached is 40° C.

The solution is kept under stirring in the darkness for 24 hours, then 10.0 ml ethylene glycol are added to eliminate all the salts and the solution is lyophilized.

28.0 g dry product are obtained.

Chemical analysis: aldehyde contents = 1.50 meq/g.

IR analysis: 2700 cm$^{-1}$, 1700 cm$^{-1}$ in addition to the pre-existing bands.

Elemental analysis Br = 35.5%.

Tests on the Antibacterial and Antifungal Activity

Using the copolymers of example 1 and example 4 tests on the bactericide, bacteriostatic, fungicide, and fungistatic activity were carried out, in comparison with the copolymers marked respectively as FCB 1010 and FCB 1011 obtained according to the process of the European Patent 0042075.

The substances were dissolved in sterile water in a 5% (wt/vol) concentration and the obtained solutions were considered as mother solutions.

All other solutions were obtained from the mother solution by dilution in a liquid culture medium of high growth capacity such as Bacto-Tryptic Soy Broth, Nutrient Broth or Sabouraud Broth (Difco).

All tests were carried out in quadruplicate on bacterial strains deriving from particularly resistant hospital strains and on fungine and yeast strains.

In particular, the following bacterial strains were used:

Bacillus subtilis
Staphylococcus aureus
Proteus vulgaris
Pseudomonas aeruginosa and the following fungine and yeast strains:

Epidermophyton floccosum
Microsporum gypseum
Aspergillus flavus
Candida albicans Inoculation 12 × 4 tubes containing 9 ml culture medium were combined serially with 1 ml 5% mother solution of the above drugs in the first dilution, and, in succession from the second to the twelfth, with 10 ml of the solution of the preceding tube.

In this way the following drug concentrations were obtained:

| Tube N. | Dilution | % |
|---|---|---|
| 1 | 1:10 | 0.5 |
| 2 | 1:20 | 0.25 |
| 3 | 1:40 | 0.125 |
| 4 | 1:80 | 0.062 |
| 5 | 1:160 | 0.031 |
| 6 | 1:320 | 0.015 |
| 7 | 1:640 | 0.007 |
| 8 | 1:1280 | 0.003 |
| 9 | 1:2560 | 0.0015 |
| 10 | 1:5120 | 0.0007 |
| 11 | 1:10240 | 0.0003 |
| 12 | 1:20480 | 0.0001 |

To each tube a constant bacterial load of $5 \times 10^5$ cells was then inoculated in sterile conditions.

A series of tubes were not inoculated and served as a "blank" against which the O.D. of the corresponding bacteria inoculated tubes were read at the spectrophotometer at 550 nm.

The bacterial activity was determined on these compounds with the turbidimetric method after 24 hours incubation at 37° C.

The test consisted in determining the values of the light transmitted by the culture media containing the test bacteria and the drug at the various concentrations, using as controls the same culture media containing only the drug to be tested at the same concentrations.

The values are given as Minimum Bacterial Concentration (MBC), that is the drug concentration which destroys 99.9% of the inoculum.

For the determination of the bacteriostatic activity, a culture fraction (0.1 ml) was inoculated taken from the tubes which presented low or no bacterial growth, in new tubes containing 10 ml fresh culture medium without the drug, and the growth capacity of the present bacteria was determined by the turbidimetric method. The Minimum Inhibiting Drug concentration (MIC) present in the first series of tubes which allowed the growth of the test bacteria in the second series of tubes containing the culture medium and no drug, after 24 hours incubation at 37° C., was considered as bacteriostatic.

RESULTS

Antibacterial Activity of the Substance FCB 1010

(expressed as concentration capable of inactivating 99.9% of the inoculum)

| | Bactericide | Bacteriostatic |
|---|---|---|
| Bacillus Subtilis | 0.006% | 0.003% |
| Staph. Aureus | 0.031% | 0.015% |
| Pr. Vulgaris | 0.5% | 0.3% |
| Ps. Aeruginosa | 0.6% | 0.31% |

Antibacterial Activity of the Substance of Example 1

(expressed as concentration capable of inactivating 99.9% of the inoculum)

| | Bactericide | Bacteriostatic |
|---|---|---|
| Bacillus Subtilis | 0.0015% | 0.0007% |
| Staph. Aureus | 0.0125% | 0.0062% |
| Pr. Vulgaris | 0.062% | 0.031% |
| Ps. Aeruginosa | 0.125% | 0.031% |

Antibacterial Activity of the Substance FCB 1011

(expressed as concentration capable of inactivating 99.9% of the inoculum)

| | Bactericide | Bacteriostatic |
|---|---|---|
| Bacillus Subtilis | 0.0062% | 0.0031% |
| Staph. Aureus | 0.025% | 0.0125% |
| Pr. Vulgaris | 0.250% | 0.125% |
| Ps. Aeruginosa | 0.250% | 0.062% |

Antibacterial Activity of the Substance of Example 4

(expressed as concentration capable of inactivating 99.9% of the inoculum)

| | Bactericide | Bacteriostatic |
|---|---|---|
| Bacillus Subtilis | 0.0015% | 0.0007% |
| Staph. Aureus | 0.0125% | 0.0062% |
| Pr. vulgaris | 0.062% | 0.031% |
| Ps. Aeruginosa | 0.125% | 0.031% |

Antifungal Activity of the Substance FCB 1010

(expressed as concentration capable of inactivating 99.9% of the inoculum)

| | Fungicide | Fungistatic |
|---|---|---|
| Epid. Floccosum | 0.125% | 0.062% |
| Micr. Gypseum | 1% | 0.5% |
| Asp. Flavus | 1% | 0.3% |
| Cand. Albicans | 0.25% | 0.125% |

Antifungal activity of the Substance of Example 1

(expressed as concentration capable of inactivating 99.9% of the inoculum)

| | Fungicide | Fungistatic |
|---|---|---|
| Epid. Floccosum | 0.031% | 0.015% |
| Micr. Gypseum | 0.031% | 0.025% |
| Asp. Flavus | 0.125% | 0.05% |
| Cand. Albicans | 0.062% | 0.031% |

Antifungal Activity of the Substance FCB 1011

(expressed as concentration capable of inactivating 99.9% of the inoculum)

| | Fungicide | Fungistatic |
|---|---|---|
| Epid. Floccosum | 0.125% | 0.03% |
| Micr. Gypseum | 0.25% | 0.06% |
| Asp. Flavus | 0.25% | 0.25% |
| Cand. Albicans | 0.25% | 0.12% |

Antifungal Activity of the Substance of Example 4

(expressed as concentration capable of inactivating 99.9% of the inoculum)

| | Fungicide | Fungistatic |
|---|---|---|
| Epid. Floccosum | 0.031% | 0.015% |
| Micr. Gypseum | 0.031% | 0.025% |
| Asp. Flavus | 0.062% | 0.031% |
| Cand. Albicans | 0.062% | 0.031% |

Toxicity Tests on the Compound of Example 1

$DI_{50}$ on Sprague Dawley rat and on Swiss mouse was higher than 4 g/Kg per os.

Protracted administrations for a 3 month period did not give evidence of any toxicity up to 1 g/Kg per os.

I claim:

1. A saccharide copolymer having antibacterial or antifungal activity of the following formula (I):

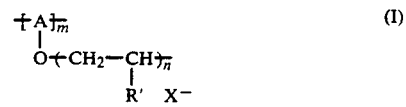

wherein:

A represents a monomeric unit selected from the group consisting of a starch and a cellulose, and wherein between 10 and 90% of said monomeric units contain two aldehyde groups, obtained by oxidative opening in the $C_2$ and $C_3$ positions of the glucoside unit;

m is an integer between 10 and 10,000;

$R^+$ is a quaternary ammonium radical selected from the group consisting of:

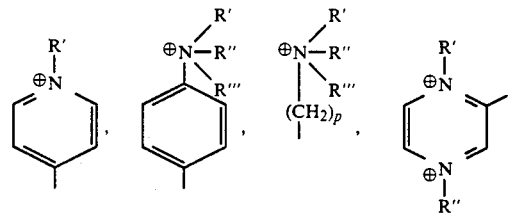

wherein R', R", and R''' are the same or different and each is an alkyl or benzyl radical, and p is zero or an integer between 1 and 10;

$X^-$ is an anion selected from the group consisting of $F^-$, $Cl^-$, $Br^-$, $I^-$, $HSO_4^-$ and $CH_3OSO_3^-$; and n is an integer between 100 and 250.

2. A pharmaceutical composition having antibacterial or antifungal activity comprising an antibacterial or antifungal effective amount of the saccharide copolymer as defined in claim 1 and a pharmaceutically acceptable carrier.

* * * * *